(12) United States Patent
Yoshioka et al.

(10) Patent No.: US 10,514,362 B2
(45) Date of Patent: Dec. 24, 2019

(54) WIRE ROPE FLAW DETECTION DEVICE

(71) Applicant: MITSUBISHI ELECTRIC CORPORATION, Tokyo (JP)

(72) Inventors: Takashi Yoshioka, Tokyo (JP); Takayuki Kotera, Tokyo (JP); Kazuaki Hirota, Tokyo (JP); Tomokazu Hoshinoo, Tokyo (JP); Fumitake Takahashi, Tokyo (JP); Masao Akashi, Tokyo (JP); Tetsuro Seki, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 8 days.

(21) Appl. No.: 15/766,160

(22) PCT Filed: Nov. 2, 2015

(86) PCT No.: PCT/JP2015/080907
§ 371 (c)(1),
(2) Date: Apr. 5, 2018

(87) PCT Pub. No.: WO2017/077570
PCT Pub. Date: May 11, 2017

(65) Prior Publication Data
US 2018/0299408 A1 Oct. 18, 2018

(51) Int. Cl.
G01N 27/87 (2006.01)
(52) U.S. Cl.
CPC .................................. G01N 27/87 (2013.01)
(58) Field of Classification Search
None
See application file for complete search history.

(56) References Cited

U.S. PATENT DOCUMENTS

2011/0006762 A1* 1/2011 Yoshioka ............... G01N 27/83
324/240
2011/0268343 A1* 11/2011 Groos ..................... G01N 27/87
382/141

FOREIGN PATENT DOCUMENTS

JP   55-48649 A    4/1980
JP   62-85856 A    4/1987
(Continued)

OTHER PUBLICATIONS

International Search Report (PCT/ISA/210) dated Jan. 26, 2016, by the Japanese Patent Office as the International Searching Authority for International Application No. PCT/JP2015/080907.
(Continued)

Primary Examiner — Clayton E. LaBalle
Assistant Examiner — Jas A Sanghera
(74) Attorney, Agent, or Firm — Buchanan Ingersoll & Rooney PC

(57) ABSTRACT

Provided is a wire rope flaw detector including a magnetizer configured to form a main magnetic flux in a part of a wire rope in a longitudinal direction thereof. A plurality of search coils are configured to detect a leakage flux that occurs from a damaged part of the wire rope in a segment in which the main magnetic flux is formed. A control unit is configured to detect induced voltages generated in the plurality of search coils. Further, the control unit is configured to superimpose voltage waveforms of the plurality of search coils on one another while shifting the voltage waveforms by a time calculated based on an interval between the plurality of search coils adjacent to each other and on a relative moving speed of the wire rope with respect to the magnetizer, to thereby amplify a peak of the induced voltage.

9 Claims, 11 Drawing Sheets

(56) References Cited

FOREIGN PATENT DOCUMENTS

| JP | 7-198684 A | 8/1995 |
| JP | 9-210968 A | 8/1997 |
| JP | 2015-166697 A | 9/2015 |

OTHER PUBLICATIONS

Written Opinion (PCT/ISA/237) dated Jan. 26, 2016, by the Japanese Patent Office as the International Searching Authority for International Application No. PCT/JP2015/080907.

* cited by examiner

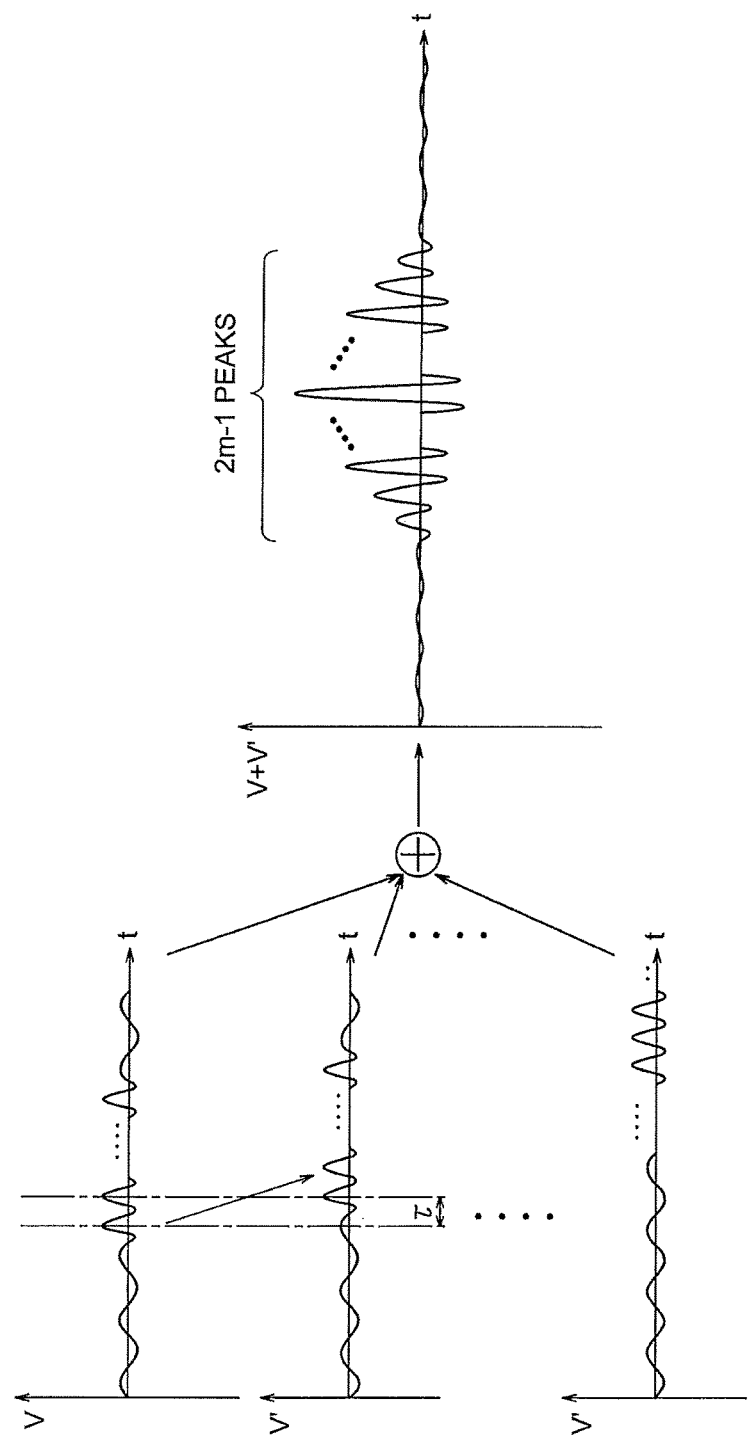

WIRE ROPE FLAW DETECTION DEVICE

TECHNICAL FIELD

The present invention relates to a wire rope flaw detector configured to detect breakage of a wire rope, for example, a wire rope for suspending a car of an elevator or a wire rope used for a crane, and a break in an element wire of the wire rope, namely, damage to the element wire.

BACKGROUND ART

In general, for a wire rope used for an elevator, a crane, or the like, it is periodically checked whether or not a break exists in an element wire. When a large number of element wires are broken, the wire rope is replaced. Such inspection is performed by visual observation as a rule, but a wire rope flaw detector may be used in order to improve work efficiency.

The related-art wire rope flaw detector includes a magnetizer and a coil portion serving as a magnetic sensor. The magnetizer includes a first permanent magnet and a second permanent magnet, which are arranged with an interval so as to be spaced apart from each other, and a back yoke configured to join the first permanent magnet and the second permanent magnet to each other. The coil portion is arranged between the first permanent magnet and the second permanent magnet.

At a time of inspection of the wire rope, the magnetizer is brought into contact with the wire rope so that the first permanent magnet and the second permanent magnet are aligned with each other in a longitudinal direction of the wire rope, and the wire rope is moved relatively with respect to the magnetizer. At this time, a segment of the wire rope between the first permanent magnet and the second permanent magnet is magnetized.

In a case where damage has been caused to the wire rope, a leakage flux occurs in a periphery of a damaged part when the damaged part enters the magnetized segment. The leakage flux is detected by the coil portion. Therefore, it is possible to determine whether or not a break exists in the element wire by measuring output from the coil portion. That is, when the leakage flux from the damaged part is interlinked with the coil portion, an induced voltage is generated at both ends of the coil portion, which enables the detection of the break in the element wire.

The coil portion includes a first search coil and a second search coil, which are arranged with an interval so as to be spaced apart from each other in a moving direction of the wire rope. Therefore, differential output between the first search coil and the second search coil is obtained, to thereby cancel a noise voltage superimposed on the first search coil and the second search coil in the same phase. Meanwhile, the induced voltage due to the break remains without being canceled because of a difference in time at which the induced voltage is generated in each of the search coils, which improves an S/N ratio (see, for example, PTL 1).

CITATION LIST

Patent Literature

[PTL 1] JP 09-210968 A

SUMMARY OF INVENTION

Technical Problem

The related-art wire rope flaw detector described above is effective for noise superimposed on the, respective search coils in the same phase, but raises a problem in that, when noise superimposed in an opposite phase occurs, the noise is emphasized and an S/N ratio deteriorates.

When a ferromagnetic material exists in the vicinity of the wire rope to be inspected, for example, when a wire rope to be inspected is arranged next to another wire rope, a component that leaks from the rope to be inspected toward the ferromagnetic material in the vicinity, returns to the rope to be inspected, and flows into the S-pole of the magnetizer occurs in a magnetic flux generated from the N-pole of a magnetizer. At this time, directions of magnetic fluxes interlinked with the first search coil and the second search coil are reverse to each other, and hence positive and negative polarities of induced voltages generated in the first search coil and the second search coil are reverse to each other.

In this case, when the first search coil and the second search coil are connected to each other in series so as to have polarities reverse to each other, the respective induced voltages of the search coils have the same polarity, which emphasizes noise.

The present invention has been made in order to solve the above-mentioned problem, and has an object to obtain a wire rope flaw detector capable of more positively improving an S/N ratio.

Solution to Problem

According to one embodiment of the present invention, there is provided a wire rope flaw detector including: a magnetizer, which is configured to form a main magnetic flux in a part of a wire rope in a longitudinal direction of the wire rope; a plurality of search coils, which are arranged with an interval so as to be spaced apart from one another in the longitudinal direction of the wire rope, and are configured to detect a leakage flux that occurs from a damaged part of the wire rope in a segment in which the main magnetic flux is formed; and a control unit, which is configured to detect induced voltages generated in the plurality of search coils, in which the control unit is configured to superimpose voltage waveforms of the plurality of search coils on one another while shifting the voltage waveforms by a time calculated based on an interval between the plurality of search coils adjacent to each other and on a relative moving speed of the wire rope with respect to the magnetizer, to thereby amplify a peak of the induced voltage.

Advantageous Effects of Invention

In the wire rope flaw detector according to the present invention, the voltage waveforms of the plurality of search coils are superimposed on each other while the voltage waveforms are shifted by the time calculated based on the interval between the plurality of search coils adjacent to each other and on the relative moving speed of the wire rope with respect to the magnetizer, to thereby amplify the peak of the induced voltage. Thus, the S/N ratio can be improved more positively.

BRIEF DESCRIPTION OF DRAWINGS

FIG. 11 is an explanatory diagram for illustrating a waveform processing method performed by a control unit of FIG. 10.

DESCRIPTION OF EMBODIMENTS

Figure 1:
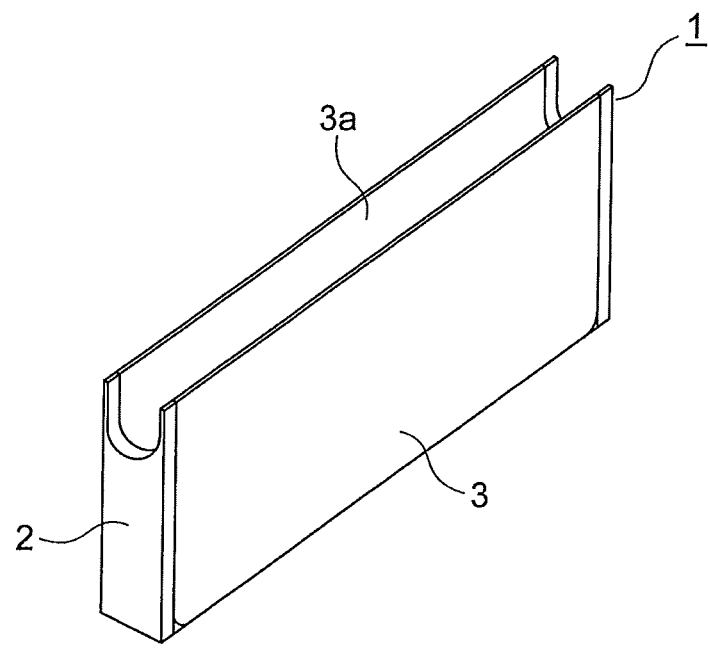
FIG. 1 is a perspective view for illustrating a probe of a wire rope flaw detector according to a first embodiment of the present invention.
Figure 2:
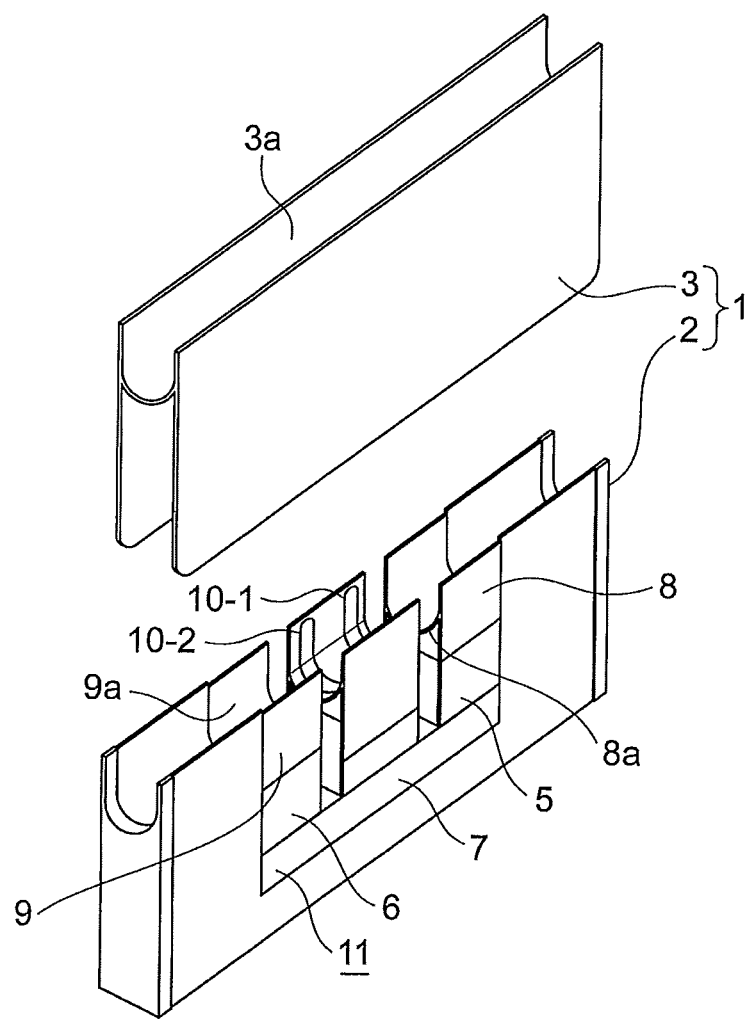
FIG. 2 is a perspective view for illustrating the probe by decomposing a part of the probe of FIG. 1.

Now, embodiments for carrying out the present invention are described with reference to the accompanying drawings.
First Embodiment FIG. 1 is a perspective view for illustrating a probe of a wire rope flaw detector according to a first embodiment of the present invention, and FIG. 2 is a perspective view for illustrating the probe by decomposing a part of the probe of FIG. 1. In the figures, a case 1 includes a case main body 2 and a cover 3 configured to cover the case main body 2 to protect components provided inside the probe. The cover 3 is provided with a cover groove portion 3a having a U-shaped section. A wire rope 4 (FIG. 3) is guided to an inside of the cover groove portion 3a, and is moved relatively with respect to the probe while kept in contact with the cover 3.

The case main body 2 includes a first permanent magnet 5, a second permanent magnet 6, a back yoke 7, a first pole piece 8, a second pole piece 9, a first search coil 10-1, and a second search coil 10-2. The first permanent magnet 5 and the second permanent magnet 6 are arranged with an interval so as to be spaced apart from each other. The back yoke 7 joins the first permanent magnet 5 and the second permanent magnet 6 to each other at end portions thereof that are located opposite to the cover groove portion 3a.

The first pole piece 8 is fixed to an end portion of the first permanent magnet 5 located on the cover groove portion 3a side. The second pole piece 9 is fixed to an end portion of the second permanent magnet 6 located on the cover groove portion 3a side. In the first pole piece 8 and the second pole piece 9, a first pole piece groove portion 8a and a second pole piece groove portion 9a each having a U-shaped section to be brought into contact with an outer surface of the cover groove portion 3a are each formed in order to cause magnetic fluxes generated in the first permanent magnet 5 and the second permanent magnet 6 to flow into the wire rope 4 with efficiency.

A magnetizer 11 includes the first permanent magnet 5, the second permanent magnet 6, the back yoke 7, the first pole piece 8, the second pole piece 9, and the cover 3. The first search coil 10-1 and the second search coil 10-2 are arranged inside a magnetic circuit formed of the first permanent magnet 5, the second permanent magnet 6, the back yoke 7, the first pole piece 8, the second pole piece 9, and the cover 3.

The first search coil 10-1 and the second search coil 10-2 are each obtained by forming a coil wound in an oval shape into a U-shape. The first search coil 10-1 and the second search coil 10-2 are arranged so as to have a positional relationship symmetrical with respect to the center of an interval between the first pole piece 8 and the second pole piece 9.

Figure 3:
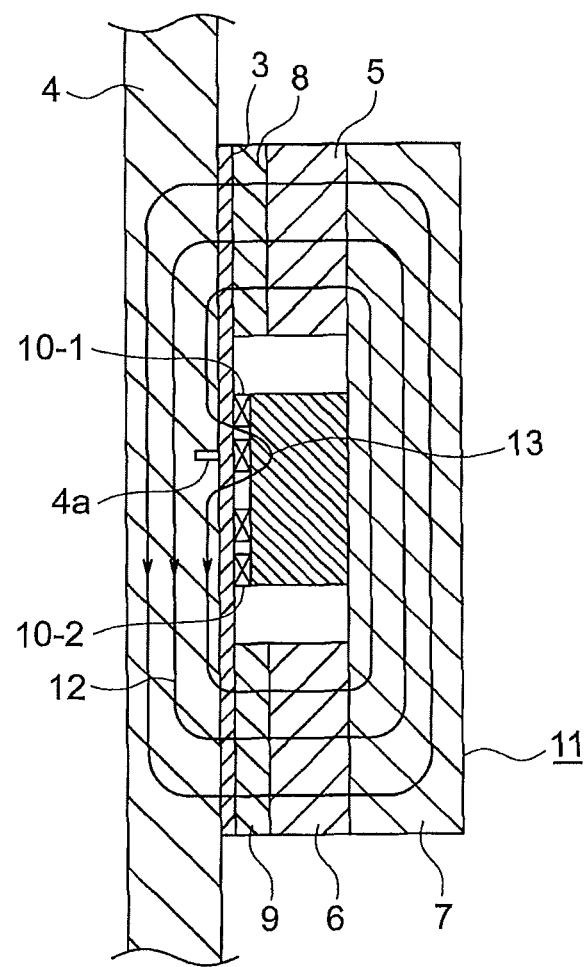
FIG. 3 is an explanatory diagram for illustrating a flaw detection principle using the probe of FIG. 1.

FIG. 3 is an explanatory diagram for illustrating a flaw detection principle using the probe of FIG. 1. At a time of inspection of the wire rope 4, the probe is placed so that the wire rope 4 is inserted into the cover groove portion 3a. With this placement, the first permanent magnet 5 and the second permanent magnet 6 are set with an interval so as to be spaced apart from each other in a longitudinal direction of the wire rope 4, and a segment of the wire rope 4 between a part opposed to the first permanent magnet 5 and a part opposed to the second permanent magnet 6 is magnetized. That is, the magnetizer 11 forms a main magnetic flux 12 in a part of the wire rope 4 in the longitudinal direction along the longitudinal direction of the wire rope 4. In this state, the wire rope 4 is moved relatively with respect to the probe.

In a case where damage has been caused to the wire rope 4, a leakage flux 13 occurs in a periphery of a damaged part 4a when the damaged part 4a enters the magnetized segment. The leakage flux 13 is detected by the first search coil 10-1 and the second search coil 10-2. The first search coil 10-1 and the second search coil 10-2 are arranged with an interval in the longitudinal direction of the wire rope 4, and hence a time difference occurs in the detection of the leakage flux 13.

Figure 4:
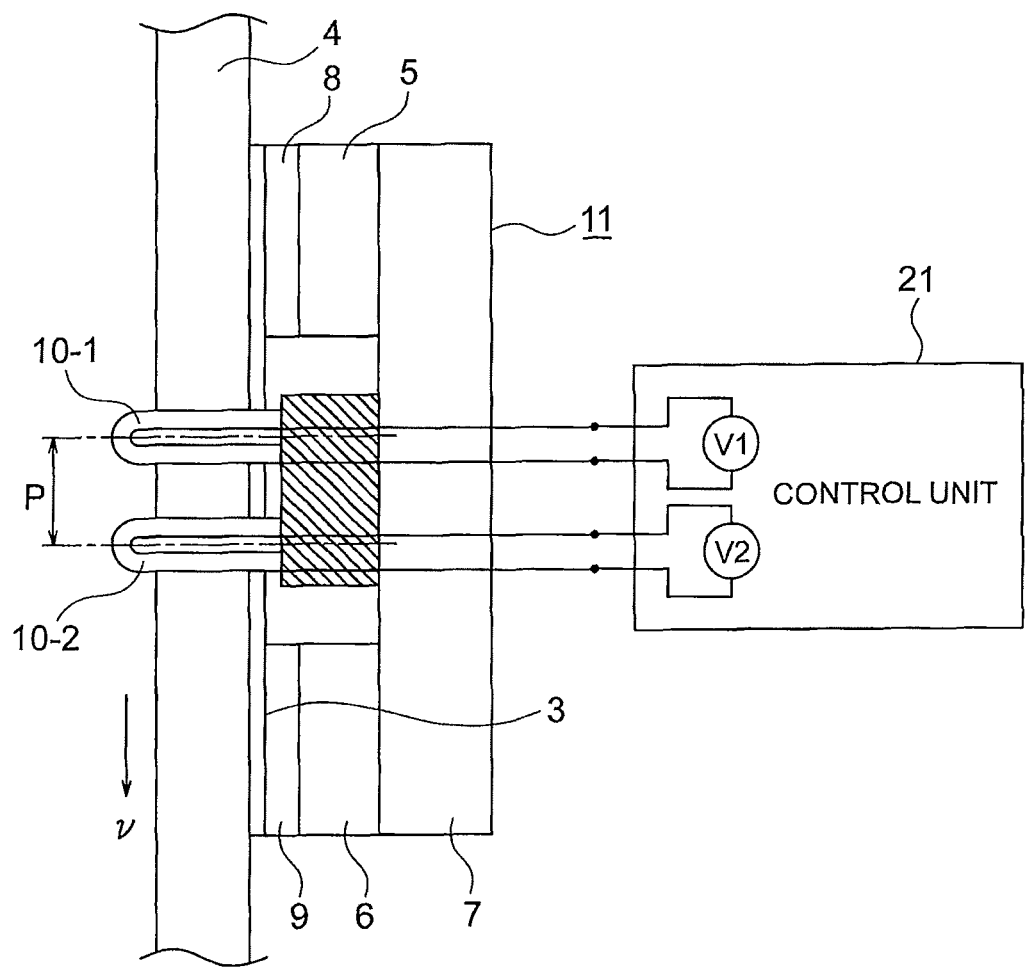
FIG. 4 is a configuration diagram for illustrating a main part of the wire rope flaw detector according to the first embodiment.

FIG. 4 is a configuration diagram for illustrating a main part of the wire rope flaw detector according to the first embodiment. The first search coil 10-1 and the second search coil 10-2 are electrically connected to a control unit 21 being a detection processing unit. The control unit 21 detects an induced voltage V1 generated at both ends of the first search coil 10-1 and an induced voltage V2 generated at both ends of the second search coil 10-2. The control unit 21 also processes waveforms of the induced voltage V1 and the induced voltage V2 to determine whether or not damage exists in the wire rope 4.

Figure 5:
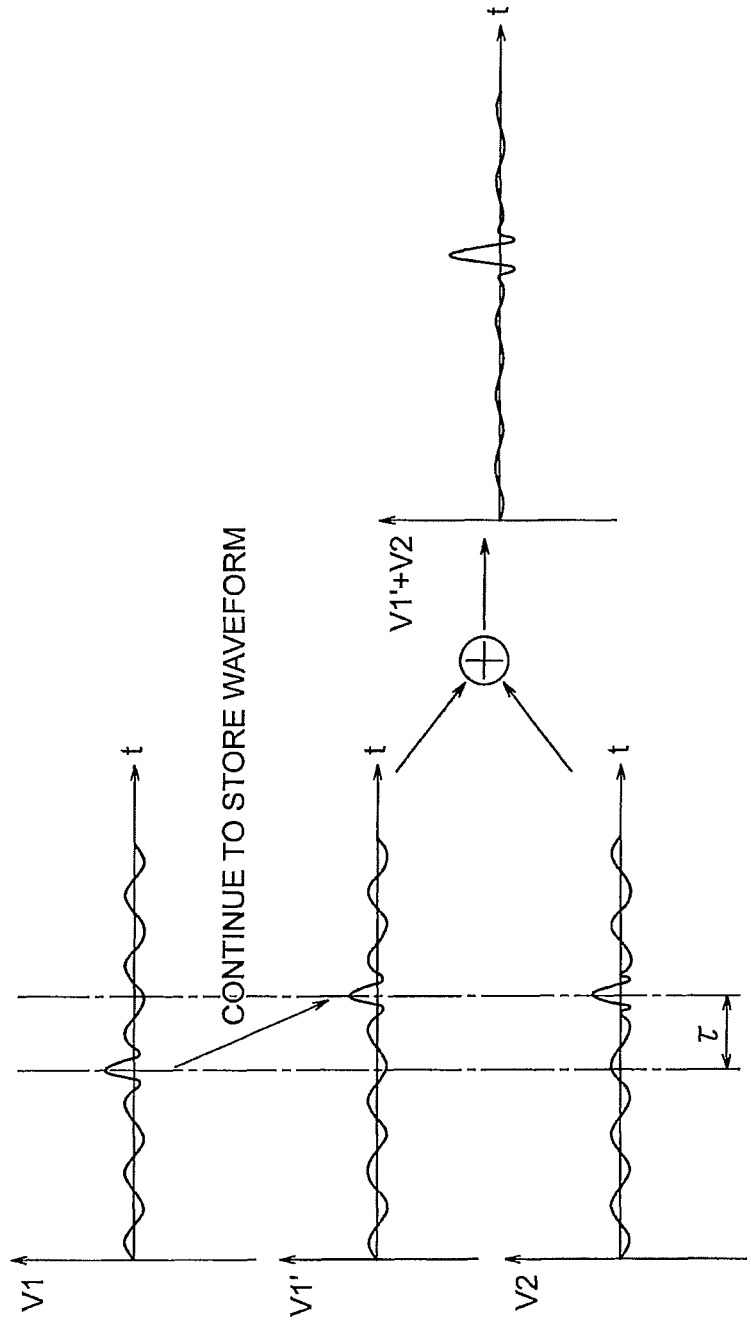
FIG. 5 is an explanatory diagram for illustrating a waveform processing method performed by a control unit of FIG. 4.

FIG. 5 is an explanatory diagram for illustrating a waveform processing method performed by the control unit 21 of FIG. 4, and is an illustration of a case in which the damaged part 4a of the wire rope 4 passes through the probe at a fixed moving speed v. In this case, P represents a distance between the center of the first search coil 10-1 and the center of the second search coil 10-2 (FIG. 4). It is also assumed that the first search coil 10-1 is positioned on upstream of the wire rope 4 in the moving direction, and the second search coil 10-2 is positioned on downstream of the wire rope 4 in the moving direction.

When the damaged part 4a enters space between the first pole piece 8 and the second pole piece 9, the leakage flux 13 (FIG. 3) occurs in the vicinity of the damaged part 4a. The leakage flux 13 is interlinked with the first search coil 10-1, and is then interlinked with the second search coil 10-2. Therefore, times at which peaks occur in the induced voltages V1 and V2 are shifted by a time period τ (=P/v) obtained by dividing the distance P by the moving speed v.

The control unit 21 includes a storage unit configured to temporarily store waveform data on the induced voltages V1 and V2. In this embodiment, the waveform data is subjected to digital sampling, and is stored in a first-in first-out (FIFO) buffer being a storage unit. The control unit 21 also superimposes (as shown in waveform on the right of FIG. 5) a waveform (waveform on the middle left of FIG. 5), which is obtained by delaying the waveform of the induced voltage V1 (waveform on the upper left of FIG. 5) preceding the induced voltage V2 by the time period τ, on the waveform of the induced voltage V2 (waveform on the lower left of FIG. 5). With the superimposition, the peaks of the induced voltages due to the damaged part 4*a* can be amplified.

Incidentally, the above-mentioned superimposition may also cause noise to be amplified. The noise is amplified most when a cycle period of the noise is represented by Tn with the above-mentioned delay time period τ being an integral multiple of Tn. At this time, the peaks of the noise are overlapped with each other to approximately double an amplitude thereof, but the amplitude of a signal is approximately doubled as well, and hence an S/N ratio thereof does not change. The amplitude of noise at a cycle period other than the above-mentioned cycle period is equal to or smaller than twice the amplitude at the time of the above-mentioned superimposition, and hence an amplification rate of the noise is smaller than an amplification rate of the signal. Therefore, the S/N ratio is improved on the whole. That is, it is possible to more positively improve the S/N ratio irrespective of respective directions of magnetic fluxes interlinked with the search coil 10-1 and the search coil 10-2.

In particular, when a given dominant periodic component exists in the noise, the above-mentioned delay time period is caused to become equal to a time period corresponding to a half of the cycle period of the noise or equal to an odd multiple of the time period, to thereby be able to cancel a dominant periodic component of the noise while amplifying the signal.

Further, the first search coil 10-1 and the second search coil 10-2 are used, thereby be able to minimize the number of coils and to suppress the cost.

In the first embodiment, the first search coil 10-1 and the second search coil 10-2 are used, but at least three search coils may be arranged at regular intervals in the longitudinal direction of the wire rope 4.

That is, when the number of search coils is represented by m being an integer equal to or larger than 2, an installation interval of the search coils is represented by P, a relative moving speed of the wire rope with respect to the magnetizer is represented by v, and the induced voltages generated in the respective search coils are represented by $V_1(t), \ldots, V_m(t)$ in order from the upstream side of the wire rope in the moving direction, the control unit may include a circuit or a processing algorithm that uses the following expression as an evaluation index S(t) of whether or not a damaged part exists. The control unit can also be formed of a circuit or a computer configured to perform the above-mentioned processing.

$$S(t) = \sum_{k=1}^{m} V_k\left(t - \frac{P}{v}(m-k)\right)$$

In this manner, with the superimposition of waveforms, the peak value of a signal is multiplied by an integer equal to the number of search coils in principle. Meanwhile, the noise does not always have the peaks overlapped with each other at the cycle period determined by a retention time period for the superimposition, and hence an increment of the noise is generally suppressed to an amount smaller than an increment of a signal. Assuming that a fixed dominant cycle period exists in the noise, it is also possible to set an installation pitch of search coils to a number obtained by multiplying the cycle period of the noise by one over an integer to select such an installation pitch of coils and such an installation number of coils as to cause noises superimposed on the respective search coils to cancel each other in accordance with phases of the noises and to cause a signal to be superimposed thereon.

Second Embodiment

Figure 6:
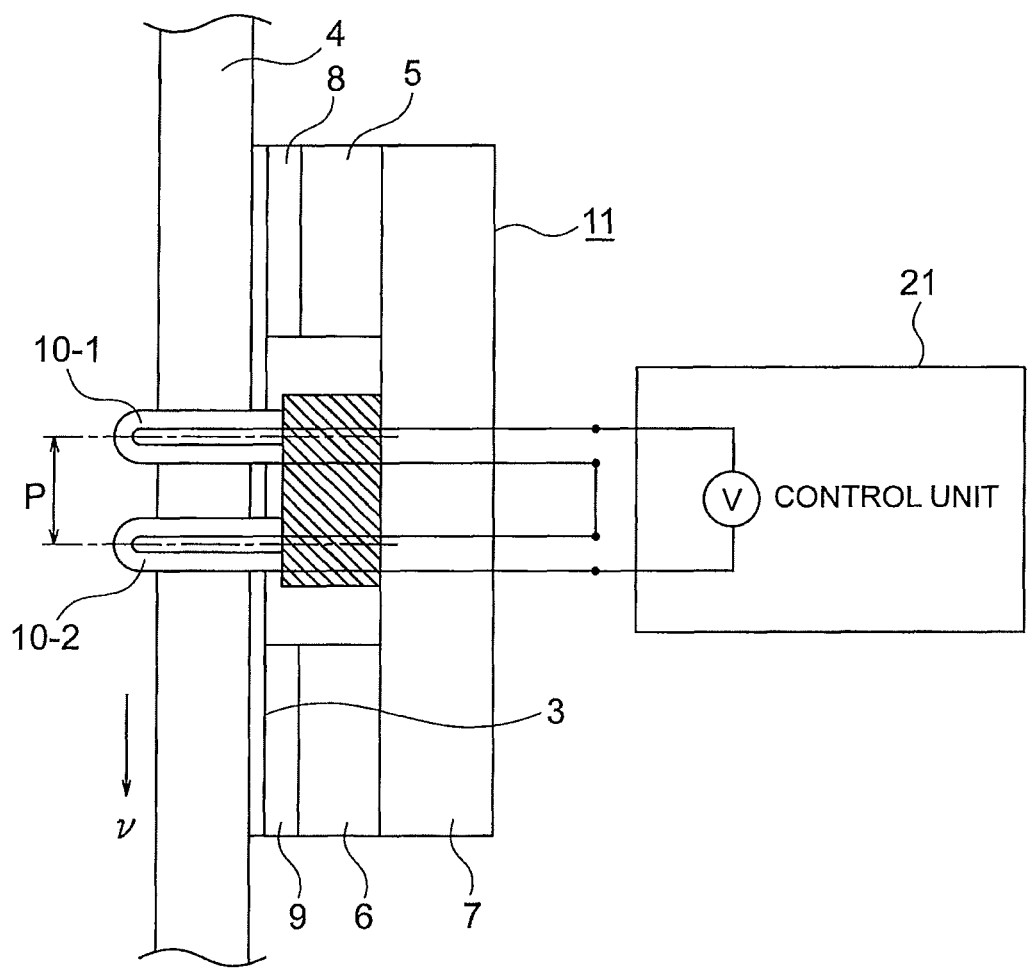
FIG. 6 is a configuration diagram for illustrating a main part of a wire rope flaw detector according to a second embodiment of the present invention.

Next, FIG. 6 is a configuration diagram for illustrating a main part of a wire rope flaw detector according to a second embodiment of the present invention. The specifications of components of the probe for magnetizing the wire rope 4, namely, the first permanent magnet 5, the second permanent magnet 6, the back yoke 7, the first pole piece 8, and the second pole piece 9, are the same as those of the first embodiment.

The second embodiment is different from the first embodiment in the signal processing method. In this embodiment, the first search coil 10-1 and the second search coil 10-2 are connected to each other in series. A difference between a potential at one end of the first search coil 10-1 and a potential at one of the second search coil 10-2 is A/D-converted in the subsequent stage to be stored in the FIFO buffer of the control unit 21 as output that combines the two search coils 10-1 and 10-2.

Figure 7:
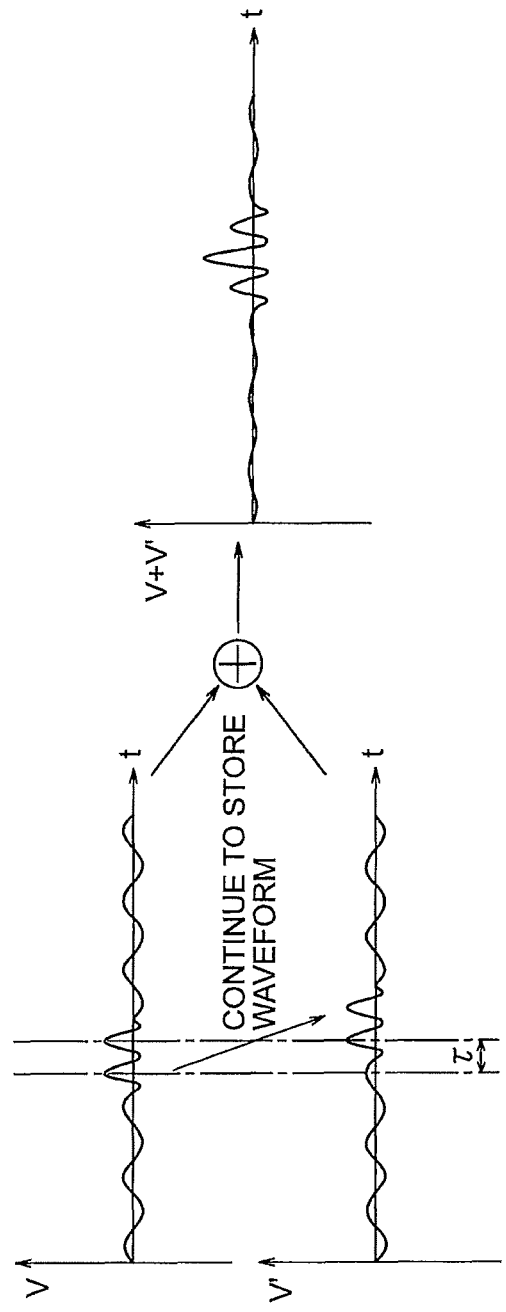
FIG. 7 is an explanatory diagram for illustrating a waveform processing method performed by a control unit of FIG. 6.

FIG. 7 is an explanatory diagram for illustrating the waveform processing method performed by the control unit 21 of FIG. 6. In the same manner as in the first embodiment, when the damaged part 4*a* passes through the space between the first pole piece 8 and the second pole piece 9, two peaks of an induced voltage V due to the leakage flux 13 (FIG. 3) are observed. The control unit 21 of this embodiment superimposes a voltage at a current time and a voltage at a time earlier by the time period τ on each other in terms of the observed waveforms. With this configuration, as illustrated in the waveform on the right of FIG. 7, three peaks of the induced voltage appear around a time at which the damaged part 4*a* passes the above-mentioned space, and a height of the second peak of those is amplified by the effect of the superimposition.

In this embodiment as well, noise is also amplified to a double level when a delay time period exhibited at a time of the superimposition of the waveforms is an integral multiple of the cycle period of the noise. However, the signal is also amplified to a double level at the same time, while the amplification rate of the noise at another cycle period is equal to or smaller than twice the amplitude, and hence the S/N ratio is improved on the whole. That is, it is possible to more positively improve the S/N ratio irrespective of the respective directions of the magnetic fluxes interlinked with the search coil 10-1 and the search coil 10-2.

Further, according to this embodiment, it is possible to suppress the load imposed on processing for calculating numerical values while suppressing the manufacturing cost. The reason is as follows. In the first embodiment, the output from the first search coil 10-1 and the output from the second search coil 10-2 are A/D converted separately from each other, while in this embodiment, the output from the first search coil 10-1 and the output from the second search coil 10-2 are combined into one by being connected to each other in series, and hence it suffices that the number of A/D-converted channels per probe is one.

In addition, in the first embodiment, in order to determine which one of the output from the first search coil 10-1 and the output from the second search coil 10-2 are is to be delayed, it is required to distinguish whether the damaged part 4a passes from the first search coil 10-1 toward the second search coil 10-2 or from the second search coil 10-2 toward the first search coil 10-1. Therefore, the moving direction is required to be manually input through some device, or it may be required to provide an encoder or other such position detection device for automatically detecting the moving direction.

However, in this embodiment, the waveforms to be superimposed are the same in shape but different in timing by the fixed time period, and hence it is not required to know the moving direction of the wire rope 4 and to provide a device for inputting the moving direction.

Figure 8:
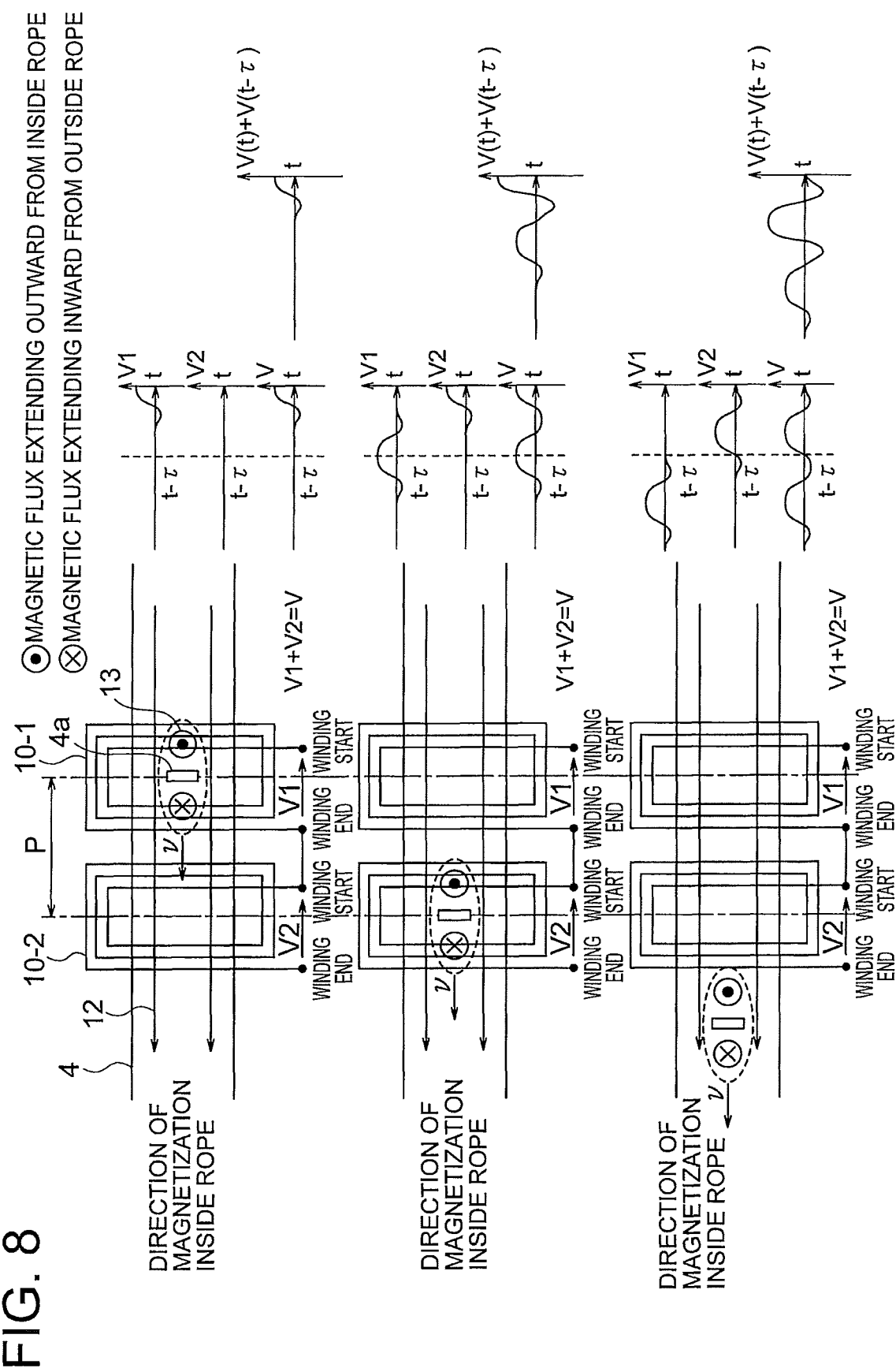
FIG. 8 is an explanatory diagram for illustrating a relationship between a movement of a leakage flux, which is exhibited when a damaged part passes through a first search coil and a second search coil that are connected to each other in a forward direction, and a waveform of a detected induced voltage.

FIG. 8 is an explanatory diagram for illustrating a relationship between a movement of the leakage flux 13, which is exhibited when the damaged part 4a passes through the first search coil 10-1 and the second search coil 10-2 of FIG. 6, and a waveform of a detected induced voltage, and is an illustration of a waveform exhibited when the first search coil 10-1 and the second search coil 10-2 are connected to each other in series so as to have the same polarity, that is, connected to each other in series in a forward direction.

FIG. 8 is also an illustration of an example in which, assuming that winding directions of the first search coil 10-1 and the second search coil 10-2 are unified as the direction of a right-hand screw when facing the wire rope 4, a terminal on a winding end side of the first search coil 10-1 and a terminal on a winding start side of the second search coil 10-2 are connected to each other in series, and a voltage between a terminal on a winding start side of the first search coil 10-1 and a terminal on a winding end side of the second search coil 10-2 is measured as output.

In a case where the wire rope 4 has been magnetized in a direction as illustrated in FIG. 8, when the damaged part 4a passes from the first search coil 10-1 toward the second search coil 10-2, the leakage flux 13 is first interlinked with the first search coil 10-1 in the direction as illustrated in FIG. 8 to generate an induced voltage. Then, the same induced voltage as that generated in the first search coil 10-1 is generated in the second search coil 10-2 later by the time period τ.

Therefore, in the case of the above-mentioned connection direction, the polarity of the peak of the induced voltage exhibited at a time of passage of the damaged part 4a is the same in both the first search coil 10-1 and the second search coil 10-2 as illustrated in FIG. 8. In view of this, when the voltage at the current time and the voltage at the time earlier by the time period τ are superimposed on each other, it is possible to emphasize the signal by summing up the two voltages that have the same sign.

When the winding directions of the first search coil 10-1 and the second search coil 10-2 are reverse to each other, terminals both at the winding start or terminals both at the winding end are connected to each other in series, to thereby be able to achieve the same direction at which induced voltages occur as that described above.

Meanwhile, there is a case in which it is advantageous to connect the first search coil 10-1 and the second search coil 10-2 to each other so as to have polarities reverse to each other depending on a relationship between a timing at which a disturbance magnetic flux being a source of noise is interlinked with each of the first search coil 10-1 and the second search coil 10-2 and an interlinked direction thereof. In this case, the coils are connected to each other in a direction reverse to the direction in the above-mentioned case of having the same polarity.

That is, when the winding directions of the first search coil 10-1 and the second search coil 10-2 are the same, a winding end terminal of the first search coil 10-1 and a winding end terminal of the second search coil 10-2 may be connected to each other, and when the winding directions are reverse to each other, the winding end terminal of the first search coil 10-1 and a winding start terminal of the second search coil 10-2 may be connected to each other.

Figure 9:
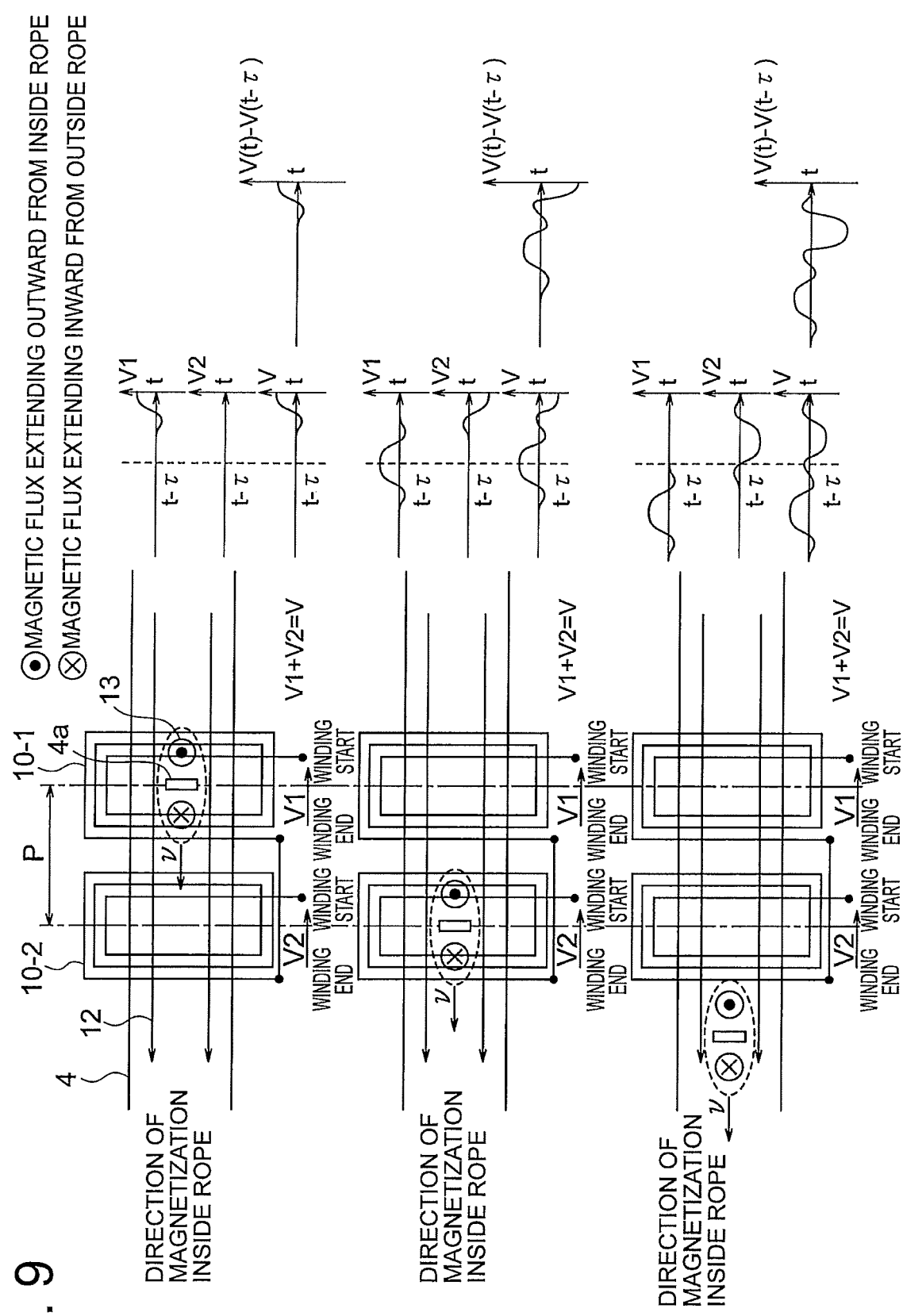
FIG. 9 is an explanatory diagram for illustrating a relationship between a movement of a leakage flux, which is exhibited when the damaged part passes through the first search coil and the second search coil that are connected to each other in a reverse direction, and a waveform of a detected induced voltage.

In this case, when the voltage at the current time and the voltage at the time earlier by the time period τ are superimposed on each other, it is possible to emphasize the signal by summing up the two voltages that have opposite signs as illustrated in FIG. 9.

Now, an example of a specific method of superimposing the voltages is described. In this embodiment, the output from the first search coil 10-1 and the output from the second search coil 10-2 connected to the first search coil 10-1 in series are sampled by an A/D converter, and a finite impulse response (FIR) filter is then applied thereto, to thereby achieve superimposition thereof. That is, a coefficient for summing up two points spaced apart from each other by the number of points corresponding to τ is set as a filter coefficient of the FIR filter.

Specifically, a filter coefficient h[n] is expressed by the following mathematical expression. In the expression, n represents an integer, and N represents the number of taps, which is a power of 2 equal to or larger than 4 in this case. Further, Δt represents a sampling interval for the A/D converter. In addition, double vertical lines sandwiching τ/2Δt means that τ/2Δt is rounded off to an integer.

$$h[n] = \begin{cases} 0 & \left(n \neq \frac{N}{2} \pm \left\|\frac{\tau}{2\Delta t}\right\|\right) \\ 1 & \left(n = \frac{N}{2} \pm \left\|\frac{\tau}{2\Delta t}\right\|\right) \end{cases} \quad \text{(Expression 1)}$$

A function exhibited when the above-mentioned filter coefficient h[n] is applied to the FIR filter is considered specifically. Assuming that an output voltage A/D-converted by the search coil is ε[k], a sequence stored in a buffer of the FIR filter at a given time is expressed by the following expression.

$$\left\{\varepsilon[k-(N-1)], \varepsilon[k+(N-2)], \ldots \varepsilon\left[k-\left(\frac{N}{2}+\left\|\frac{\tau}{2\Delta t}\right\|-1\right)\right], \right. \quad \text{(Expression 2)}$$
$$\left. \ldots, \varepsilon\left[k-\left(\frac{N}{2}-\left\|\frac{\tau}{2\Delta t}\right\|-1\right)\right], \ldots, \varepsilon[k]\right\}$$

When the above-mentioned sequence is multiplied by the filter coefficient h[n]={0, . . . 0, 1, 0, . . . , 0, 1, 0 . . . 0}, filter output y[k] at the given time is expressed by the following expression.

$$y[k] = \varepsilon\left[k-\left(\frac{N}{2}+\left\|\frac{\tau}{2\Delta t}\right\|-1\right)\right] + \varepsilon\left[k-\left(\frac{N}{2}-\left\|\frac{\tau}{2\Delta t}\right\|-1\right)\right] \quad \text{(Expression 3)}$$

An interval between the first term and the second term on the right-hand side is expressed by the following numerical value.

$$2\left\|\frac{\tau}{2\Delta t}\right\|$$

The above-mentioned interval corresponds to the time period τ required by the wire rope 4 to pass through the space between the search coil 10-1 and the search coil 10-2. As a result, it is understood that a sum of output at a given time and output earlier than the given time by the time period τ can be obtained by the filter coefficient h[n] of the FIR filter.

Now, consideration is given to a frequency characteristic of h[n]. Assuming that a discrete Fourier transform of h[n] is H(k) with Expression 2-1 and Expression 3-1 being established, Expression 4 is obtained.

$$W^{nk} = e^{-j\frac{2\pi}{N}} \quad \text{(Expression 2-1)}$$

$$\eta = \left\|\frac{\tau}{2\Delta t}\right\| \quad \text{(Expression 3-1)}$$

$$|H(k)| = \left|\sum_{n=1}^{N} h[n]W^{kn}\right| = \quad \text{(Expression 4)}$$

$$\left|W^{k\left(\frac{N}{2}-\eta\right)} + W^{k\left(\frac{N}{2}+\eta\right)}\right| = \left|W^{k\frac{N}{2}}(W^{-k\eta} + W^{k\eta})\right| =$$

$$\left|2e^{-j\pi k}\cos\frac{2\pi\eta}{N}k\right| = \left|2\cos\frac{2\pi\eta}{N}k\right|$$

From the above-mentioned expressions, |H(k)| is 0 when Expression 5 is established, and is the maximum value 2 when Expression 6 is established. In the expressions, γ represents an integer (0, 1, 2 . . . ).

$$k = \frac{N}{4\eta}(1 + 2\gamma) \quad \text{(Expression 5)}$$

$$k = \frac{N\gamma}{2\eta} \quad \text{(Expression 6)}$$

Incidentally, when a stepping width on a frequency axis for the discrete Fourier transform is represented by Δf, the following relationship is generally established.

$$N = \frac{1}{\Delta f \Delta t} \quad \text{(Expression 7)}$$

When Expression 3-1 and Expression 7 are each substituted into Expression 5 and Expression 6 to be modified, Expression 5 and Expression 6 are expressed as follows.

$$\text{(Expression 5)} \Leftrightarrow k\Delta f = \frac{1}{2\eta\Delta t}\left(\frac{1}{2}+\gamma\right) \cong \frac{1}{\tau}\left(\frac{1}{2}+\gamma\right) \quad \text{(Expression 8)}$$

$$\text{(Expression 6)} \Leftrightarrow k\Delta f = \frac{1}{2\mu\Delta t}\gamma \cong \frac{1}{\tau}\gamma \quad \text{(Expression 9)}$$

The left-hand sides of Expression 8 and Expression 9 represent frequencies exhibited when |H(k)| is the minimum value 0 and the maximum value 2, respectively. According to those expressions, |H(k)| takes the minimum value 0 for a frequency being ½ of the reciprocal 1/τ of the time period τ during which the wire rope passes through a coil pitch P and a frequency obtained by adding an integral multiple of 1/τ thereto, and takes the maximum value 2 for a frequency being an integral multiple of 1/τ. It is understood from this fact that, when the damaged part 4a passes through the search coil 10-1 and the search coil 10-2 at a constant speed, two peak waveforms that appear with an interval of the time period τ due to the series connection are emphasized.

When noise containing a given dominant periodic component is superimposed on the output from the search coil, the coil pitch P=τv is set so that the point with |H(k)| described above being 0 falls in the vicinity of the frequency, to thereby be able to further improve the S/N ratio.

For example, a frequency corresponding to indentation pitches of strands of the wire rope 4 is conceivable as a possible example of a periodic noise component. Now, when the pitch between the indentations is set as Ps, noise having a cycle period Ps/v is assumed to occur in the output from the search coil due to the indentations. Therefore, when the point with |H(k)| described above being 0 is caused to match the frequency v/Ps of the noise, the coil pitch may be set to, for example, $$\frac{v}{2P} = \frac{v}{P_s} \Leftrightarrow P = \frac{P_s}{2} \quad \text{(Expression 10)}$$

That is, the coil pitch may be set to a half of the pitch between the indentations of the strands. In actuality, the pitch between the indentations of the strands slightly varies due to manufacturing variations of the wire rope 4, a stretch of the wire rope 4, and other such factor. However, as long as the frequency of the noise falls within a frequency range of the frequency ±θ/4P from the point with |H(k)| being 0, a segment corresponding to the frequency range is a cutoff frequency region of |H(k)|, and hence a noise reduction effect is generally obtained.

The above-mentioned specific example is given of the method of superimposition performed when the search coil 10-1 and the search coil 10-2 are connected to each other in the forward direction. Meanwhile, when the search coil 10-1 and the search coil 10-2 are connected to each other in a reverse direction, the filter coefficient h[n] is obtained as follows.

$$h[n] = \begin{cases} 0 & \left(n \neq \frac{N}{2} \pm \left\|\frac{\tau}{2\Delta t}\right\|\right) \\ -1 & \left(n = \frac{N}{2} - \left\|\frac{\tau}{2\Delta t}\right\|\right) \\ 1 & \left(n = \frac{N}{2} + \left\|\frac{\tau}{2\Delta t}\right\|\right) \end{cases} \quad \text{(Expression 11)}$$

At this time, the output y[k] is expressed by the following expression.

$$y[k] = \quad \text{(Expression 12)}$$

$$-\varepsilon\left[k - \left(\frac{N}{2} + \left\|\frac{\tau}{2\Delta t}\right\| - 1\right)\right] + \varepsilon\left[k - \left(\frac{N}{2} - \left\|\frac{\tau}{2\Delta t}\right\| - 1\right)\right]$$

The frequency characteristic of h[n] is also expressed as follows.

$$|H(k)| = \left|\sum_{n=1}^{N} h[n]W^{kn}\right| = \quad \text{(Expression 13)}$$

$$\left|W^{k(\frac{N}{2}-\eta)} - W^{k(\frac{N}{2}+\eta)}\right| = \left|W^{k\frac{N}{2}}(W^{-k\eta} - W^{k\eta})\right| =$$

$$\left|-2e^{-j\pi k}j\sin\frac{2\pi\eta}{N}k\right| = \left|2\sin\frac{2\pi\eta}{N}k\right|$$

From the above-mentioned expressions, |H(k)| is 0 when Expression 14 given below is established, and is the maximum value 2 when Expression 15 given below is established. In the expressions, γ represents an integer (0, 1, 2 . . . ).

$$k = \frac{N}{2\eta}\gamma \quad \text{(Expression 14)}$$

$$k = \frac{N}{4\eta}(1 + 2\gamma) \quad \text{(Expression 15)}$$

That is, |H(k)| takes 0 for a frequency being an integral multiple of the reciprocal 1/τ of the time period τ during which the wire rope 4 passes through the coil pitch, and takes the maximum value 2 for ½ of the frequency and a frequency obtained by adding an integral multiple of 1/τ thereto. It is understood from this fact that two peak waveforms generated in phases opposite to each other with the interval of the time period τ due to the series connection are emphasized.

In this manner, even in a case where the search coil 10-1 and the search coil 10-2 are connected to each other in the reverse direction, when the noise containing a given dominant periodic component is superimposed on the output from the search coil, the coil pitch P is set so that the point with |H(k)| described above being 0 is caused to fall in the vicinity of the frequency, to thereby be able to further improve the S/N ratio.

Further, as in the case of the forward direction, a frequency corresponding to a pitch between indentations of strands of the wire rope 4 is conceivable as a possible example of a periodic noise component. Now, when the pitch between the indentations is set as Ps, noise having a cycle period Ps/v is assumed to occur in the output from the search coil due to the indentations. Therefore, when the point with |H(k)| described above being 0 is caused to match the frequency v/Ps of the noise, the coil pitch may be set to, for example, $$\frac{v}{P} = \frac{v}{P_s} \Leftrightarrow P = P_s \quad \text{(Expression 16)}$$

That is, the coil pitch may be set to the same pitch as that of the indentations of the strands. In actuality, the pitch between the indentations of the strands slightly varies due to manufacturing variations of the wire rope 4, a stretch of the wire rope 4, and other such factor. However, as long as the frequency of the noise falls within a frequency range of the frequency ±v/4P from the point with |H(k)| being 0, a segment corresponding to the frequency range is a cutoff frequency region of |H(k)|, and hence a noise reduction effect is generally obtained.

Third Embodiment

Figure 10:
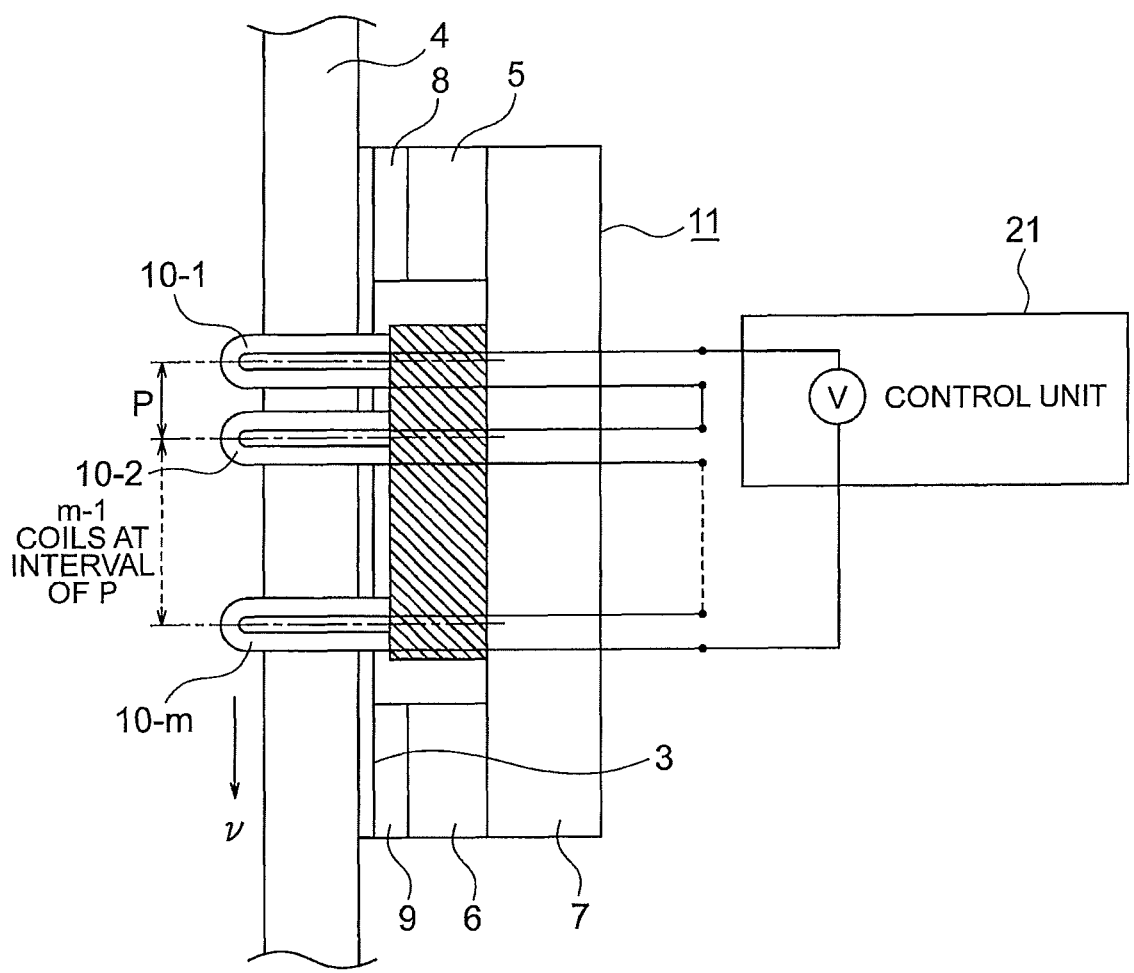
FIG. 10 is a configuration diagram for illustrating a main part of a wire rope flaw detector according to a third embodiment of the present invention.

Next, FIG. 10 is a configuration diagram for illustrating a main part of a wire rope flaw detector according to a third embodiment of the present invention, and FIG. 11 is an explanatory diagram for illustrating the waveform processing method performed by the control unit 21 of FIG. 10. This embodiment is achieved by generalizing the superimposition of signals described in the second embodiment with the number of search coils being set to m (m is an integer equal to or larger than 3). That is, first to m-th search coils 10-1 to 10-m are arranged in the probe at a regular interval P.

Those search coils 10-1 to 10-m are connected to one another in series, and generate m peak waveforms while one damaged part 4a passes through the probe. The peak is emphasized by superimposing those peaks m−1 times with an interval of the time period τ. Now, assuming that all the search coils 10-1 to 10-m are wound in the same direction and connected to one another in an in-phase direction, it is understood based on the same consideration as that of the second embodiment that the frequency with |H(k)| being 0 the frequency with is kΔf described below, which is a frequency being 1/m of the frequency 1/τ and a frequency obtained by adding an integral multiple of 1/τ thereto.

$$k\Delta f = \frac{1}{\tau}\left(\frac{1}{m} + \gamma\right)$$

Through use of those properties, it is possible to enhance the signal while selectively attenuating a specific noise frequency.

That is, when the respective search coils are connected to one another in series in order in terms of the moving direction of the wire rope, the control unit is provided with a function of storing V(t) for a fixed time period, where V(t) represents a voltage generated between terminals of the search coils located at both ends of the wire rope in the moving direction, each of which is not connected to the adjacent search coil. When the number of search coils is represented by m being an integer equal to or larger than 2, the installation interval of the search coils is represented by P, and the relative moving speed of the wire rope with respect to the magnetizer is represented by τ, the control unit also includes a circuit or a processing algorithm that uses the following expression as the evaluation index S(t) of whether or not the damaged part exists.

$$S(t) = \sum_{k=1}^{m} V\left(t - \frac{P}{v}(k-1)\right)$$

When an integer is represented by α, the control unit causes an amplitude response of a frequency response to waveform processing performed with V(t) as input and S(t) as output to have a local minimum point within a frequency range expressed by the following expression.

$$\frac{v}{P}\left(\frac{1}{m} + \alpha\right) \pm \frac{v}{4P}$$

In the above-mentioned example, the magnetizer 11 including the permanent magnet 5 and the permanent magnet 6 is described, but an electromagnet may be used in place of the permanent magnet 5 and the permanent magnet 6.

The invention claimed is:

1. A wire rope flaw detector, comprising:
   a magnetizer, which is configured to form a main magnetic flux in a part of a wire rope in a longitudinal direction of the wire rope;
   a plurality of search coils, which are arranged with an interval so as to be spaced apart from one another in the longitudinal direction of the wire rope, and are configured to detect a leakage flux that occurs from a damaged part of the wire rope in a segment in which the main magnetic flux is formed; and
   a control unit, which is configured to detect induced voltages generated in the plurality of search coils, wherein:
   the plurality of search coils are adjacent to each other with an interval of a half of a pitch between indentations of strands of the wire rope due to twisting of the strands; and
   the control unit is configured to superimpose voltage waveforms of the plurality of search coils on one another while shifting the voltage waveforms by a time calculated based on the interval between the plurality of search coils adjacent to each other and on a relative moving speed of the wire rope with respect to the magnetizer, to thereby amplify a peak of the induced voltage.

2. The wire rope flaw detector according to claim 1, wherein the control unit is configured to use, as an evaluation index S(t) of whether or not the damaged part exists, the following expression:

$$S(t) = \sum_{k=1}^{m} V_k\left(t - \frac{P}{v}(m-k)\right)$$

where m being an integer equal to or larger than 2 represents a number of the plurality of search coils, P represents an installation interval of the plurality of search coils, v represents the relative moving speed of the wire rope with respect to the magnetizer, and $V_1(t), \ldots, V_m(t)$ represent the induced voltages generated in the respective plurality of search coils in order from an upstream side of the wire rope in a moving direction of the wire rope.

3. The wire rope flaw detector according to claim 2, wherein m is equal to 2.

4. A wire rope flaw detector comprising:
   a magnetizer, which is configured to form a main magnetic flux in a part of a wire rope in a longitudinal direction of the wire rope;
   a plurality of search coils, which are arranged with an interval so as to be spaced apart from one another in the longitudinal direction of the wire rope, and are configured to detect a leakage flux that occurs from a damaged part of the wire rope in a segment in which the main magnetic flux is formed; and
   a control unit, which is configured to detect induced voltages generated in the plurality of search coils, wherein:
   the control unit is configured to superimpose voltage waveforms of the plurality of search coils on one another while shifting the voltage waveforms by a time calculated based on the interval between the plurality of search coils adjacent to each other and on a relative moving speed of the wire rope with respect to the magnetizer, to thereby amplify a peak of the induced voltage;
   the plurality of search coils are connected to one another in series in order in terms of a moving direction of the wire rope; and
   the control unit is configured to store V(t) for a fixed time period, and to use, as an evaluation index S(t) of whether or not the damaged part exists, the following expression:

$$S(t) = \sum_{k=1}^{m} V\left(t - \frac{P}{v}(k-1)\right)$$

where V(t) represents a voltage generated between terminals of ones of the plurality of search coils that are located at both ends of the wire rope in the moving direction, each of the terminals being not connected to an adjacent one of the plurality of search coils, m being an integer equal to or larger than 2 represents a number of the plurality of search coils, P represents an installation interval of the plurality of search coils, and v represents the relative moving speed of the wire rope with respect to the magnetizer.

5. The wire rope flaw detector according to claim 4, wherein:
   the plurality of search coils are connected to one another in series in order in terms of the moving direction of the wire rope; and
   the control unit is configured to cause an amplitude response of a frequency response to waveform processing performed with V(t) as input and S(t) as output to have a local minimum point within a frequency range expressed by the following expression:

$$\frac{v}{P}\left(\frac{1}{m} + \alpha\right) \pm \frac{v}{4P}$$

where V(t) represents a voltage generated between terminals of ones of the plurality of search coils that are located at both ends of the wire rope in the moving direction, each of the terminals being not connected to an adjacent one of the plurality of search coils, m being an integer equal to or larger than 2 represents a number of the plurality of search coils, P represents an installation interval of the plurality of search coils, v represents the relative moving speed of the wire rope with respect to the magnetizer, α represents an integer, and S(t) represents an evaluation index of whether or not the damaged part exists,
   S(t) being a sum of V(t), which is the voltage between both ends of the plurality of search coils connected to one another in series, and a waveform obtained by shifting V(t) by kτ, where τ=P/v, representing a time period during which the wire rope passes through a segment corresponding to an integral multiple kP, where k represents an integer, of an installation interval P of the plurality of search coils adjacent to each other,
   the waveform processing performed with V(t) as input and S(t) as output being the following processing for summing up a given waveform V(t) and a waveform V(t-kτ) obtained by delaying the given waveform V(t) by a fixed time period determined based on P and v:

$$S(t) = \sum_{k=1}^{m} V\left(t - \frac{P}{v}(k-1)\right)$$

where k is allowed to take a plurality of integers.

6. The wire rope flaw detector according to claim 5, wherein m is equal to 2.

7. The wire rope flaw detector according to claim 4, wherein m is equal to 2.

8. A wire rope flaw detector, comprising:
- a magnetizer, which is configured to form a main magnetic flux in a part of a wire rope in a longitudinal direction of the wire rope;
- a plurality of search coils, which are arranged with an interval so as to be spaced apart from one another in the longitudinal direction of the wire rope, and are configured to detect a leakage flux that occurs from a damaged part of the wire rope in a segment in which the main magnetic flux is formed; and
- a control unit, which is configured to detect induced voltages generated in the plurality of search coils, wherein:
- the control unit is configured to superimpose voltage waveforms of the plurality of search coils on one another while shifting the voltage waveforms by a time calculated based on the interval between the plurality of search coils adjacent to each other and on a relative moving speed of the wire rope with respect to the magnetizer, to thereby amplify a peak of the induced voltage;
- the plurality of search coils are connected to one another in series in order in terms of a moving direction of the wire rope; and
- the control unit is configured to cause an amplitude response of a frequency response to waveform processing performed with V(t) as input and S(t) as output to have a local minimum point within a frequency range expressed by the following expression:

$$\frac{v}{P}\left(\frac{1}{m} + \alpha\right) \pm \frac{v}{4P}$$

where V(t) represents a voltage generated between terminals of ones of the plurality of search coils that are located at both ends of the wire rope in the moving direction, each of the terminals being not connected to an adjacent one of the plurality of search coils, m being an integer equal to or larger than 2 represents a number of the plurality of search coils, P represents an installation interval of the plurality of search coils, v represents the relative moving speed of the wire rope with respect to the magnetizer, α represents an integer, and S(t) represents an evaluation index of whether or not the damaged part exists, S(t) being a sum of V(t), which is the voltage between both ends of the plurality of search coils connected to one another in series, and a waveform obtained by shifting V(t) by kτ, where τ=P/v, representing a time period during which the wire rope passes through a segment corresponding to an integral multiple kP, where k represents an integer, of an installation interval P of the plurality of search coils adjacent to each other, the waveform processing performed with V(t) as input and S(t) as output being the following processing for summing up a given waveform V(t) and a waveform V(t-kτ) obtained by delaying the given waveform V(t) by a fixed time period determined based on P and v:

$$S(t) = \sum_{k=1}^{m} V\left(t - \frac{P}{v}(k-1)\right)$$

where k is allowed to take a plurality of integers.

9. The wire rope flaw detector according to claim 8, wherein m is equal to 2.

* * * * *